(12) United States Patent
Schlichte et al.

(10) Patent No.: US 7,875,244 B2
(45) Date of Patent: Jan. 25, 2011

(54) GAS SENSOR WITH AT LEAST ONE CATALYTIC MEASURING ELEMENT

(75) Inventors: Mladen Schlichte, Lübeck (DE); Erik Stender, Reinfeld (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 227 days.

(21) Appl. No.: 12/132,154

(22) Filed: Jun. 3, 2008

(65) Prior Publication Data

US 2009/0016934 A1    Jan. 15, 2009

(30) Foreign Application Priority Data

Jul. 13, 2007   (DE) .................. 10 2007 032 700

(51) Int. Cl.
| G01N 7/00 | (2006.01) |
| G01N 21/00 | (2006.01) |
| G01N 27/00 | (2006.01) |
| G01N 31/00 | (2006.01) |
| G01N 33/00 | (2006.01) |

(52) U.S. Cl. .............. 422/83; 422/94; 422/98; 436/91; 436/139; 436/149; 73/23.2; 73/31.06

(58) Field of Classification Search ............ 422/94, 422/98, 83
See application file for complete search history.

(56) References Cited

U.S. PATENT DOCUMENTS

| 4,352,099 A | 9/1982 | Christen et al. |
| 5,601,693 A | 2/1997 | Davies |
| 6,548,024 B1 * | 4/2003 | Doncaster et al. ............. 422/88 |
| 6,607,642 B1 * | 8/2003 | Kiesele et al. ............. 204/415 |
| 2002/0085956 A1 * | 7/2002 | Miller et al. .................. 422/94 |
| 2006/0032745 A1 * | 2/2006 | Davies et al. ............... 204/431 |

FOREIGN PATENT DOCUMENTS

| DE | 3343159 | 6/1986 |
| DE | 38 10 409 A1 | 2/1989 |
| EP | 00 16 351 B1 | 10/1980 |
| GB | 1536305 A | 12/1978 |
| JP | 11237355 A | 8/1999 |
| JP | 2002116173 A | 4/2002 |
| WO | WO 00 43 765 A1 | 7/2000 |

* cited by examiner

*Primary Examiner*—Brian J Sines
(74) *Attorney, Agent, or Firm*—McGlew and Tuttle, P.C.

(57) ABSTRACT

A gas sensor has shock resistance and temperature resistance attributes. The gas sensor includes at least one catalytic measuring element (3), which is arranged in a sensor housing (1) forming a combustion chamber (2). The sensor housing (1) has at least one gas-permeable housing opening (4) for the gas exchange between the environment and the combustion chamber (2). The catalytic measuring element (3) is arranged between at least two disk-shaped support elements (5) made of a heat-insulating and temperature-resistant material.

20 Claims, 2 Drawing Sheets

GAS SENSOR WITH AT LEAST ONE CATALYTIC MEASURING ELEMENT

CROSS REFERENCE TO RELATED APPLICATIONS

This application claims the benefit of priority under 35 U.S.C. §119 of German Patent Application DE 10 2007 032 700.7 filed Jul. 13, 2007, the entire contents of which are incorporated herein by reference.

FIELD OF THE INVENTION

The present invention pertains to a gas sensor with at least one catalytic measuring element.

BACKGROUND OF THE INVENTION

A gas sensor with a heated gas-sensitive semiconductor as a measuring element is disclosed in DE 38 10 409 A1. The measuring element is embedded according to this document directly in a gas-permeable, heat-insulating cover in order to reduce the release of heat and to reduce the energy consumption in this manner. In addition, the sensor as a whole is said to be stabilized and made largely insensitive to mechanical effects such as shocks.

An essential drawback of this arrangement is the poorer diffusion of the gas to be measured compared to the prior-art arrangements with support wires and catalytic measuring elements arranged thereon, i.e., especially heat tone sensors called Pellistors. The cover of the measuring elements represents an additional diffusion barrier. The drawbacks become obvious especially in case of measuring high-boiling gases such as nonane or xylene. This is due both to the response time and the sensitivity of the correspondingly covered gas sensors being markedly poorer than without a cover.

Another gas sensor with poor accessibility of the gas to be measured to the catalytic measuring elements is described in U.S. Pat. No. 5,601,693.

SUMMARY OF THE INVENTION

There is a need for a gas sensor that is improved in terms of its measuring properties with at least one catalytic measuring element in a sensor housing and with a gas-permeable housing opening for the entry of gases to be measured, whose concentration can be measured by controlled combustion.

The object of the present invention is, in particular, to make available a gas sensor with at least one catalytic measuring element, which gas sensor is less sensitive to temperature changes, on the one hand, and, on the other hand, additionally ensures a good gas exchange with the environment while shock resistance is improved at the same time.

According to the invention, a gas sensor is provided comprising a sensor housing forming a combustion chamber. The sensor housing has at least one gas-permeable housing opening for a gas exchange between the environment and the combustion chamber. A catalytic measuring element is arranged in the sensor housing. Two disk-shaped support elements are provided made of a heat-insulating and temperature-resistant material. The catalytic measuring elements are arranged between the two disk-shaped support elements.

The measuring element is mechanically supported and protected from heat due to the catalytic measuring element being arranged between the at least two disk-shaped support elements made of a heat-insulating and temperature-resistant material. The diffusion or the entry of the gas to be measured is at the same time hardly hindered compared to a gas sensor with complete jacketing according to the state of the art.

Combustion products as a consequence of the controlled catalytic combustion can leave the combustion chamber more easily, as a consequence of which gas exchange with the environment is improved and at the same time there is a good fresh gas supply to the measuring elements. Better gas exchange also means that the measuring sensitivity for gases and vapors to be measured is improved, so that the signal-to-noise ratio is improved as well.

Measurements have shown that the typical response times (t-90 time) of the fully encapsulated sensor arrangements are approximately 15 sec for methane and approximately 10 minutes for high-boiling hydrocarbons such as nonane. Contrary to this, the typical response times (t-90 times) of the sensor arrangements according to the present invention likewise equal 15 sec for methane but less than 60 sec for nonane.

The methane-to-nonane sensitivity ratio, which theoretically ideally equals 1.0, is about 6 to 8 in the case of a sensor arrangement covered on all sides, has a markedly improved ratio of about 4 to 5 in the gas sensor according to the present invention.

The support elements may be arranged essentially in parallel to one another. The support elements are preferably circular. The support elements may each advantageously comprise a mat of glass fibers or ceramic fibers. The support elements may advantageously be disposed directed essentially at right angles to the housing opening. Each of the support elements may advantageously comprise a material having a density of less than $0.5$ g/cm$^3$. Each of the support elements may advantageously have a thickness greater than 0.01 mm.

The gas-permeable housing opening may advantageously comprise a metallic or ceramic sintered element. The gas-permeable housing opening may be an explosion protection element. The explosion protection element may comprise a metallic grid.

Another measuring element may be provided with each of the catalytic measuring element and the another measuring element comprising a Pellistor. The catalytic measuring element and the another catalytic measuring element may be arranged in a bridge circuit wherein the another measuring element is not provided with a catalyst promoting the measured gas-specific combustion and is connected as a compensating element.

The another measuring element and the catalytic measuring element may be arranged, together with an associated one of the support elements, in a chamber of a bracket. Each chamber of a bracket may be open towards the combustion chamber.

An exemplary embodiment of the present invention will be explained below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENT

Figure 1:
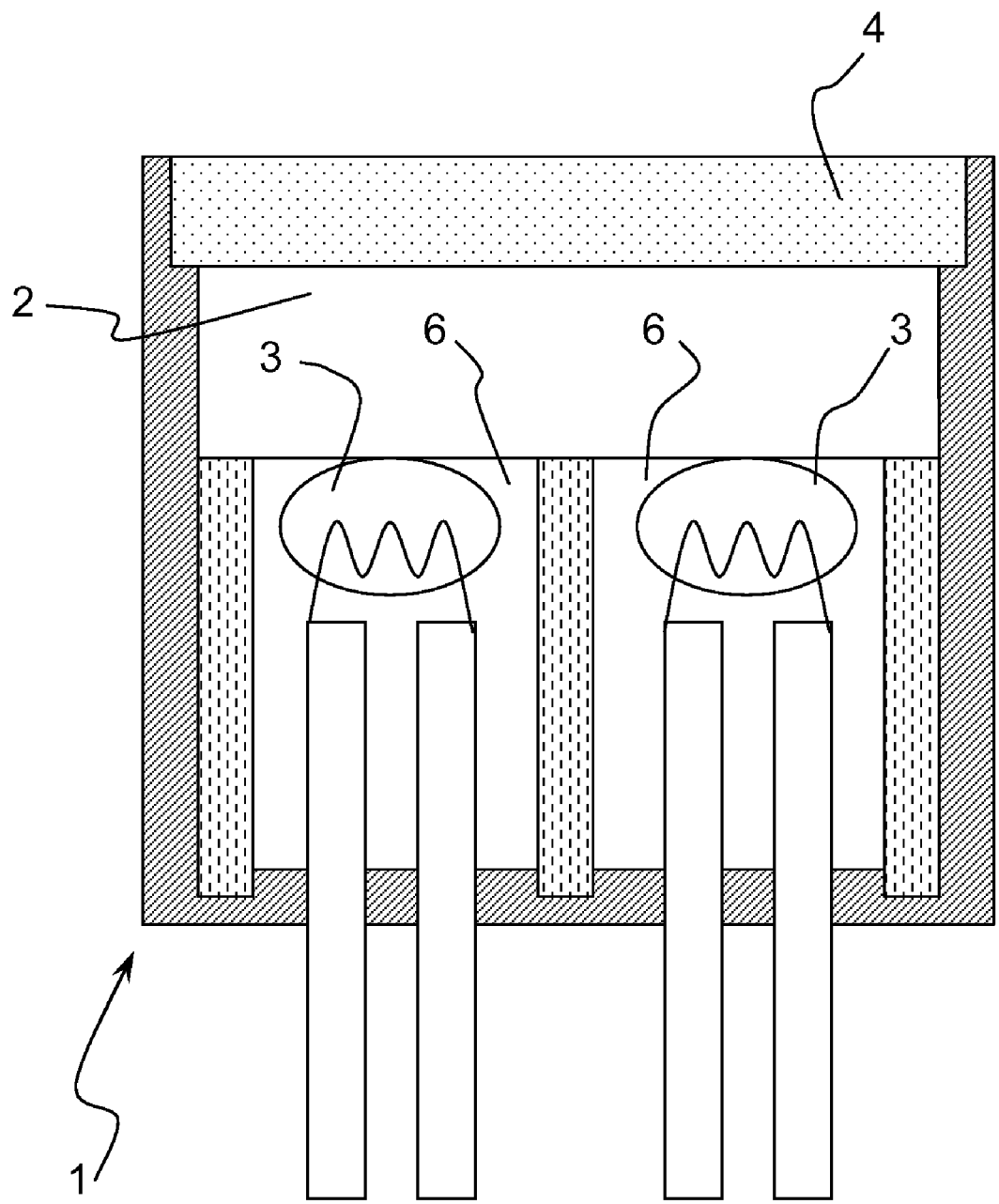
FIG. 1 is a sectional view through a gas sensor with two catalytic measuring elements, wherein one measuring element is used as a compensating element in a bridge circuit (known per se)
Figure 2:
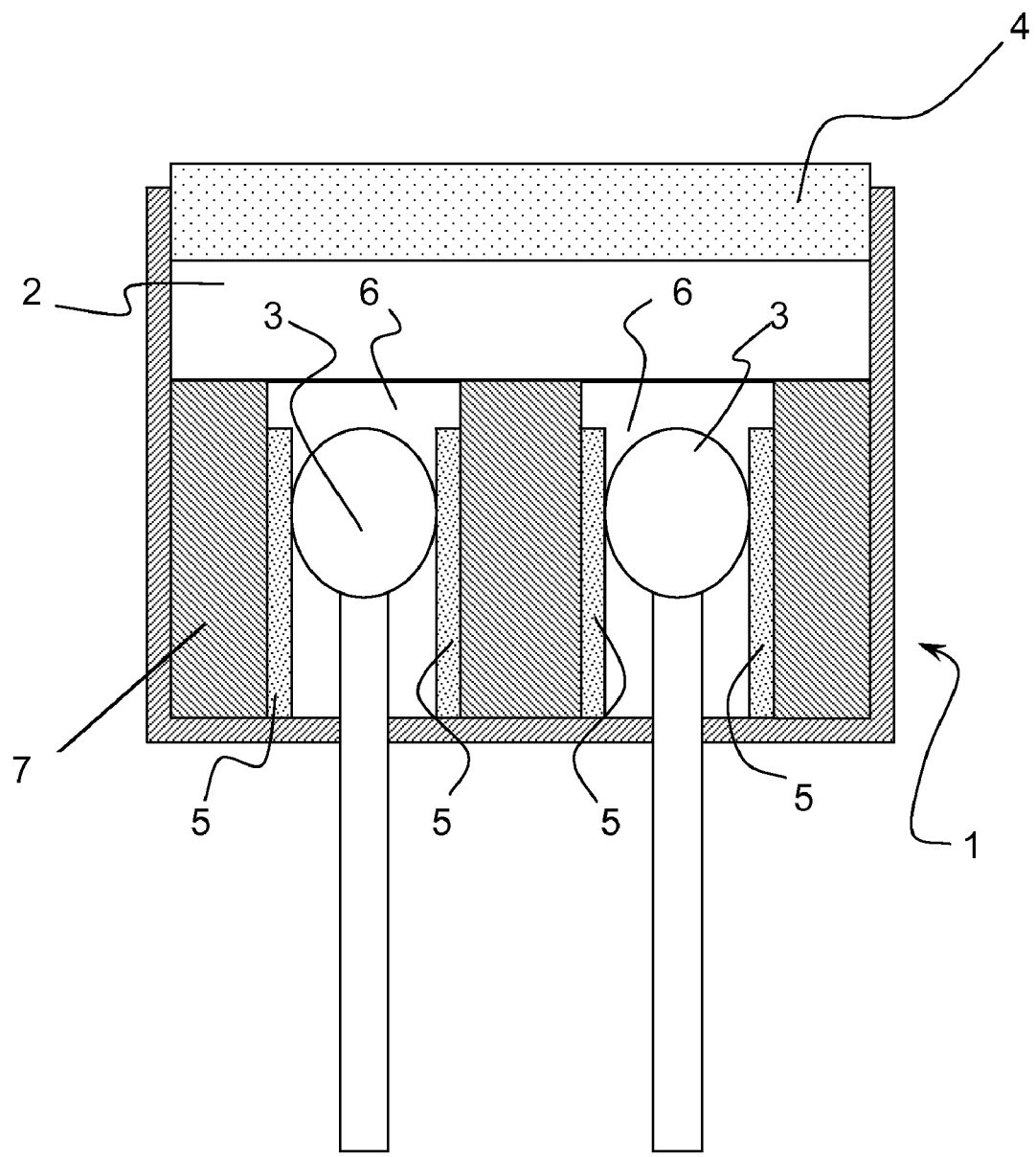
FIG. 2 is a sectional view through the gas sensor rotated by 90° compared to FIG. 1.

Referring to the drawings in particular, two measuring elements 3 designed as Pellistors are located in the preferably metallic sensor housing 1 with the housing opening element 4 made as a gas-permeable metallic or ceramic sintered element for the gas exchange with the environment. Only one of the otherwise identical measuring elements 3 is provided with a catalyst characteristic of the controlled combustion of the gas or gases to be measured. The sintered element 4 is used at the same time as a flame arrester and may also consist of a wire cloth. The metallic or ceramic sintered gas-permeable housing opening element 4 may be an explosion protection element. The explosion protection element may comprise a metallic grid.

A Pellistor is used in one of the two measuring elements 3 (the catalytic measuring element) for the catalytic oxidation to detect the gas or gases to be measured. The other, otherwise identical Pellistor without catalyst (another measuring element 3) is used as a compensating element for the detecting Pellistor. The measuring elements 3 are held in a shock-absorbed manner by means of support elements 5. The support elements 5 are arranged at least opposite each other. The support elements 5 consist of glass fiber mat with a density of less than 0.5 g/cm$^3$ and a thickness of less than 1 mm. Chambers 6 are each formed of a bracket made of a plastic. The chambers 6 are open towards the combustion chamber 2, wherein no structure is disposed between the measuring elements 3 and the combustion chamber 2.

The support elements 5 are preferably directed essentially at right angles to the housing opening element 4. This arrangement is in order to make possible a good diffusion of the gases to be measured to the measuring elements 3 and to make possible good convection of combustion products formed to the combustion chamber 2 and hence to the environment.

The improved gas exchange means that the measuring sensitivity for gases and vapors to be measured is improved. The signal-to-noise ratio is likewise improved as a result.

The temperature-resistant plastic used for the chambers 6 and the bracket is, for example, polysulfone.

It is apparent that the measuring elements 3 are connected to a suitable analyzing circuit (e.g., in a bridge circuit, wherein one of the, otherwise identical measuring elements 3 (another measuring element) is not provided with a catalyst promoting the measured gas-specific combustion and is connected as a compensating element) by means of corresponding support wires or contact elements, which lead out of the sensor housing 1.

The support elements are shown arranged essentially in parallel to one another advantageously disposed directed essentially at right angles to the housing opening. The support elements are circular in the preferred embodiment and each are formed of a mat of glass fibers or ceramic fibers. Each of the support elements comprise a material having a density of less than 0.5 g/cm$^3$. Each of the support elements may advantageously have a thickness greater than 0.01 mm.

While a specific embodiment of the invention has been shown and described in detail to illustrate the application of the principles of the invention, it will be understood that the invention may be embodied otherwise without departing from such principles.

What is claimed is:

1. A gas sensor comprising:
    a sensor housing forming a combustion chamber, said sensor housing having at least one gas-permeable housing opening for a gas exchange between the environment and said combustion chamber;
    a catalytic measuring element arranged in said sensor housing; and
    two disk-shaped support elements formed of a heat-insulating and temperature-resistant material, said catalytic measuring element being arranged between said two disk-shaped support elements, said support elements being arranged in parallel to one another, each of said support elements comprising a mat of glass fibers or ceramic fibers.

2. A gas sensor in accordance with claim 1, wherein said support elements are disposed directed essentially at right angles to said housing opening.

3. A gas sensor in accordance with claim 1, wherein each of said support elements comprise a material having a density of less than 0.5 g/cm$^3$.

4. A gas sensor in accordance with claim 1, wherein each of said support elements has a thickness greater than 0.01 mm.

5. A gas sensor in accordance with claim 1, wherein said gas-permeable housing opening comprises a metallic or ceramic sintered element.

6. A gas sensor in accordance with claim 1, wherein said gas-permeable housing opening comprises an explosion protection element.

7. A gas sensor in accordance with claim 6, wherein said explosion protection element comprises a metallic grid.

8. A gas sensor in accordance with claim 1, further comprising another measuring element, each of said catalytic measuring element and said another measuring element comprising a Pellistor, said catalytic measuring element and said another catalytic measuring element being arranged in a bridge circuit wherein said another measuring element is not provided with a catalyst promoting the measured gas-specific combustion and is connected as a compensating element.

9. A gas sensor in accordance with claim 1, further comprising another measuring element wherein each of said another measuring element and said catalytic measuring element is arranged, together with an associated one of said support elements, in a chamber of a bracket, each said chamber of a bracket being open towards said combustion chamber, said another measuring element being in direct communication with said combustion chamber, wherein no structure is disposed between said another measuring element and said combustion chamber.

10. A gas sensor in accordance with claim 1, wherein said support elements are circular.

11. A gas sensor in accordance with claim 1, wherein said two disk-shaped support elements define a catalytic measuring element space, said catalytic measuring element being arranged in said catalytic measuring element space, said catalytic measuring element being in direct communication with said combustion chamber, wherein no structure is disposed between said catalytic measuring element and said combustion chamber.

12. A gas sensor comprising:
    a sensor housing forming at least a portion of a combustion chamber, said sensor housing having an opening region and having a gas-permeable housing opening element in said opening region for a gas exchange between the environment and said combustion chamber;
    a catalytic measuring element arranged in said sensor housing;

a first disk-shaped support element comprising a heat-insulating and temperature-resistant material; and a second disk-shaped support element comprising a heat-insulating and temperature-resistant material, said catalytic measuring element being arranged between said first disk-shaped support element and said second disk-shaped support element, said first disk-shaped support element and said second disk-shaped support element defining an open side, said catalytic measuring element being in direct communication with said combustion chamber via said open side, wherein no structure extends along said open side and no structure is disposed between said combustion chamber and said catalytic measuring element.

13. A gas sensor in accordance with claim 12, wherein said first disk-shaped support element and said second disk-shaped support element are arranged essentially in parallel to one another and each comprise a mat of glass fibers or ceramic fibers.

14. A gas sensor in accordance with claim 13, wherein:
each of said support elements comprise a material having a density of less than 0.5 g/cm$^3$; and
each of said support elements have a thickness greater than 0.01 mm.

15. A gas sensor comprising:
a sensor housing with an open end;
a catalytic measuring element arranged in said sensor housing;
another measuring element arranged in said sensor housing adjacent to said catalytic measuring element;
a gas-permeable housing element closing said open end of said sensor housing, said sensor housing and said gas-permeable housing element cooperating to form a combustion chamber in a region above said catalytic measuring element and above said another measuring element, said gas-permeable housing element for a gas exchange between a sensor housing environment and said combustion chamber;
a first disk-shaped support element comprising a heat-insulating and temperature-resistant material;
a second disk-shaped support element comprising a heat-insulating and temperature-resistant material, said catalytic measuring element being arranged between said first disk-shaped support element and said second disk-shaped support element, said catalytic measuring element being one of disposed adjacent to said combustion chamber and at a spaced location from said combustion chamber, said catalytic measuring element being exposed to said combustion chamber, wherein no structure is disposed between said catalytic measuring element and said combustion chamber;
a third disk-shaped support element comprising a heat-insulating and temperature-resistant material; and
a fourth disk-shaped support element comprising a heat-insulating and temperature-resistant material, said another measuring element being arranged between said third disk-shaped support element and said fourth disk-shaped support element, said another measuring element being one of disposed adjacent to said combustion chamber and at a spaced location from said combustion chamber, said another measuring element being exposed to said combustion chamber, wherein no structure is disposed between said another measuring element and said combustion chamber.

16. A gas sensor in accordance with claim 15, wherein said first disk-shaped support element, said second disk-shaped support element, said third disk-shaped support element and said fourth disk-shaped support element are arranged essentially in parallel to one another, each of said first disk-shaped support element, said second disk-shaped support element, said third disk-shaped support element and said fourth disk-shaped support element comprising a mat of glass fibers or ceramic fibers.

17. A gas sensor in accordance with claim 16, wherein each of said support elements is disposed directed essentially at right angles to said housing opening.

18. A gas sensor in accordance with claim 16, wherein said gas-permeable housing element comprises a metallic or ceramic sintered element.

19. A gas sensor in accordance with claim 16, wherein said gas-permeable housing opening comprises an explosion protection element.

20. A gas sensor in accordance with claim 16, further comprising a bracket defining a first sensor chamber open side towards said combustion chamber and a second sensor chamber open side towards said combustion chamber, wherein no structure extends along said first sensor chamber open side and no structure extends along said second sensor chamber open side, said catalytic measuring element being disposed in said first chamber together with said first disk-shaped support element and said second disk-shaped support element and said another measuring element being disposed in said second chamber together with said third disk-shaped support element and said fourth disk-shaped support element, each of said catalytic measuring element and said another measuring element comprising a Pellistor.

* * * * *